(12) United States Patent
Rüdenauer et al.

(10) Patent No.: US 10,150,730 B2
(45) Date of Patent: Dec. 11, 2018

(54) PROCESS FOR PREPARING α-DAMASCONE

(71) Applicant: BASF SE, Ludwigshafen am Rhein (DE)

(72) Inventors: Stefan Rüdenauer, Weinheim (DE); Thomas Fenlon, Mannheim (DE); Shrirang Hindalekar, Mumbai (IN); Nisha Pansare, Navi Mumbai (IN); Abhijeet Deb Roy, Thane (IN); Vijay Narayanan Swaminathan, Ludwigshafen (DE)

(73) Assignee: BASF SE, Ludwigshafen am Rhein (DE)

(*) Notice: Subject to any disclaimer, the term of this patent is extended or adjusted under 35 U.S.C. 154(b) by 0 days.

(21) Appl. No.: 15/753,244

(22) PCT Filed: Aug. 17, 2016

(86) PCT No.: PCT/EP2016/069489
§ 371 (c)(1),
(2) Date: Feb. 16, 2018

(87) PCT Pub. No.: WO2017/029313
PCT Pub. Date: Feb. 23, 2017

(65) Prior Publication Data
US 2018/0244613 A1   Aug. 30, 2018

(30) Foreign Application Priority Data
Aug. 18, 2015 (EP) .................................... 15181406

(51) Int. Cl.
*C07C 45/39* (2006.01)
*C07C 403/16* (2006.01)
*C07C 49/203* (2006.01)

(52) U.S. Cl.
CPC ............ *C07C 403/16* (2013.01); *C07C 45/39* (2013.01); *C07C 49/203* (2013.01); *C07C 2601/16* (2017.05)

(58) Field of Classification Search
CPC .... C07C 45/39; C07C 403/16; C07C 409/203
See application file for complete search history.

(56) References Cited

FOREIGN PATENT DOCUMENTS

DE  1807568 A1  6/1969
GB  1240309 A   7/1971

OTHER PUBLICATIONS

International Prelminary Report on Patentability for PCT/EP2016/069489 dated Jul. 21, 2017.
International Search Report for PCT/EP2016/069489 dated Oct. 24, 2016.
Liu, J., et al., "Iron-Catalyzed Aerobic Oxidation of Allylic Alcohols: The Issue of C=C Bond Isomerization", Organic Letters, vol. 15, No. 20, (2013), pp. 5150-5153.
Nakatani, Y., et al., Novelle Synthèse de l'α-Damascone, Agricultural and Biological Chemistry, vol. 38, No. 7, (1974), pp. 1351-1354.
Written Opinion of the International Searching Authority for PCT/EP2016/069489 dated Oct. 24, 2016.

*Primary Examiner* — Sikarl A Witherspoon
(74) *Attorney, Agent, or Firm* — Drinker Biddle & Reath LLP

(57) ABSTRACT

The present invention relates to a process for preparing 1-(2,6,6-trimethylcyclohex-2-en-1-yl)but-2-en-1-one, which comprises a) providing 6,10-dimethylundeca-1,5,9-trien-4-ol, b) oxidizing 6,10-dimethylundeca-1,5,9-trien-4-ol provided in step a) with an oxidizing agent in the presence of at least one organic nitroxyl radical, at least one nitrate compound and an inorganic solid to yield 6,10-dimethylundeca-1,5,9-trien-4-one, c) reacting the 6,10-dimethylundeca-1,5,9-trien-4-one obtained in step b) with an acid to yield 1-(2,6,6-trimethylcyclohex-2-en-1-yl)but-2-en-1-one.

15 Claims, No Drawings

PROCESS FOR PREPARING α-DAMASCONE

CROSS-REFERENCE TO RELATED APPLICATIONS

This application is a national stage application (under 35 U.S.C. § 371) of PCT/EP2016/069489, filed Aug. 17, 2016, which claims benefit of European Application No. 15181406.8, filed Aug. 18, 2015, both of which are incorporated herein by reference in their entirety.

The present invention relates to a process for producing 1-(2,6,6-trimethylcyclohex-2-en-1-yl)but-2-en-1-one (α-damascone), which comprises providing 6,10-dimethylundeca-1,5,9-trien-4-ol, oxidizing 6,10-dimethylundeca-1,5,9-trien-4-ol with an oxidizing agent to 6,10-dimethylundeca-1,5,9-trien-4-one and reacting the 6,10-dimethylundeca-1,5,9-trien-4-one with an acid.

BACKGROUND OF THE INVENTION 1-(2,6,6-trimethylcyclohex-2-en-1-yl)but-2-en-1-one (α-damascone) is a aroma substance that is found in a variety of essential oils. Due to its characteristic organoleptic properties, α-damascone is of great commercial interest as fragrance or as flavor. In particular, α-damascone is widely used as fragrance chemical in deodorants and perfumes.

Today, the vast majority of the demanded α- or β-damascone, respectively, is produced synthetically from unsaturated aldehydes or ketones, e.g. from citral, cyclocitral or cyclogeranic acid, which are available in large amounts from natural and/or petrochemical sources.

There is a demand for novel processes that allow the efficient production of 1-(2,6,6-trimethylcyclohex-2-en-1-yl)but-2-en-1-one (α-damascone), e.g. by making use of mild reaction conditions to improve the yield and reduce the formation of unwanted by-products.

The synthesis of α-damascone was frequently described in the art.

DE1807568 for instance describes, besides the synthesis of other compounds, a process for the synthesis of 1-(2,6,6-trimethylcyclohex-2-en-1-yl)but-2-en-1-one (α-damascone) starting from 3,7-Dimethylocta-2,6-dienal (citral) mainly through two different routes. Route 1 comprises the reaction of α-cyclocitral (2,6,6-trimethylcaclohex-2-ene-1-carbaldehyde), obtained via the cyclization of citral, with 1-propenylmagnesiumbromide to the alcohol (E)-1-(2,6,6-trimethylcyclohex-2-en-1-yl)but-2-en-1-ol, which is then oxidized to α-damascone using chromium trioxide or manganese dioxide. Route 2 comprises the reaction of citral with 1-propenylmagnesiumbromide to 6,10-dimethyl-2,5,9-trien-4-ol, which is oxidized with manganese dioxide to the corresponding ketone 6,10-dimethyl-2,5,9-trien-4-one (pseudo damascone). The pseudo damascone is then cyclized to α-damascone using boron trifluoride diethyl etherate. For the oxidation of the alcohol intermediates to the corresponding ketones, silver acetate, oxygen containing derivatives of transition metal elements, in particular chromium trioxide, manganese dioxide or permangenate, and gaseous molecular oxygen are mentioned as suitable oxidizing agents.

Nakatani et al., Agr. Biol. Chem., 1974, Vol. 38(7), pp. 1351-1354, describe a process for the synthesis of α-damascone starting from citral, which first comprises the reaction of citral with allylmagnesium bromide to the alcohol 6,10-dimethyl-2,5,10-trien-4-ol, which is oxidized with chromium trioxide in the presence of pyridine or 3,5-dimethyl pyrazole to the corresponding ketone 6,10-dimethyl-2,5,10-trien-4-one. This ketone is then isomerized with potassium tert-butanolate to 6,10-dimethyl-2,5,9-trien-4-one (pseudo damascone). The thus obtained pseudo-damascone is finally cyclized to α-damascone using a mineral acid, in particular phosphoric acid, or a lewis acid, in particular tin tetrachloride.

The iron catalyzed aerobic oxidation of allylic alcohols is also described in the art.

Liu et al., Org. Lett., 2013, Vol. 15, pp. 5150-5153, describe the oxidation of several allylic alcohols, such as geraniol or (E)-4-methylhept-4-ene-3-ol, with molecular oxygen in the presence of catalytic amounts of $Fe(NO_3)_3$, (2,2,6,6-Tetramethylpiperidin-1-yl)oxyl (TEMPO) and NaCl.

The vast majority of the known synthetic processes, which aim for the synthesis of α-damascone from citral, proceed via the formation of allylic alcohol intermediates, which are oxidized to the corresponding ketones. The oxidation of these allylic alcohol intermediates typically suffer from low yields, due to the formation of side products, when strong oxidants, such as chromium trioxide or potassium permanganate, are used and/or suffer from long reaction times, in particular if mild oxidants, such as manganese dioxide or molecular oxygen, are applied. Furthermore, these processes often require an additional isomerization step in order to arrive at the desired α-damascone, which further lowers the overall yield.

Due to the unsatisfactory overall yields, these processes are unsuitable for the effective production of α-damascone from citral, in particular for technical scale production.

SUMMARY OF THE INVENTION

It is therefore an object of the present invention to provide an improved process for the production of 1-(2,6,6-trimethylcyclohex-2-en-1-yl)but-2-en-1-one (α-damascone), e.g. from the readily available precursor 3,7-Dimethylocta-2,6-dienal (citral), in high overall yields. The process should be simple and efficient and should use mild reaction conditions to allow an economic production of α-damascone on technical scales. Furthermore, expensive and/or hazardous reagents should be avoided.

It was surprisingly found that 1-(2,6,6-trimethylcyclohex-2-en-1-yl)but-2-en-1-one (α-damascone) can be prepared in high yields via the oxidation of 6,10-dimethylundeca-1,5,9-trien-4-ol, with an oxidizing agent in the presence of at least one organic nitroxyl radical, at least one nitrate compound and an inorganic solid, followed by the cyclization and in situ izomerization of the thus obtained 6,10-dimethylundeca-1,5,9-trien-4-one using an acid.

Therefore, the present invention relates to a process for preparing 1-(2,6,6-trimethylcyclohex-2-en-1-yl)but-2-en-1-one, which comprises a) providing 6,10-dimethylundeca-1,5,9-trien-4-ol,
b) oxidizing 6,10-dimethylundeca-1,5,9-trien-4-ol provided in step a) with an oxidizing agent in the presence of at least one organic nitroxyl radical, at least one nitrate compound and an inorganic solid to yield 6,10-dimethylundeca-1,5,9-trien-4-one,
c) reacting the 6,10-dimethylundeca-1,5,9-trien-4-one obtained in step b) with an acid to yield 1-(2,6,6-trimethylcyclohex-2-en-1-yl)but-2-en-1-one.

The process is efficient and allows the production of 1-(2,6,6-trimethylcyclohex-2-en-1-yl)but-2-en-1-one (α-damascone) in high space-time yields in only three steps starting from a cheap and readily available precursor. The present process uses mild reaction conditions, which reduces the amount of by-products. The use of expensive and/or hazardous reagents is avoided. The technical applicability of the process is simple and inexpensive. By using the process according to the present invention, α-damascone can be provided without difficulty on industrial scales.

DETAILED DESCRIPTION 1-(2,6,6-trimethylcyclohex-2-en-1-yl)but-2-en-1-one (α-damascone) is a compound of the following formula (I):

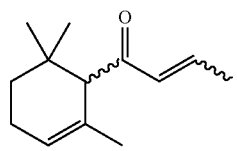

(I)

It is apparent from formula (I) that the carbon atom of the 1-position of the cyclohexane ring, which carries the crotonyl group (2-butenoyl group), may have (R)- or (S)-configuration. Furthermore, the C—C-double bond of the crotonyl group may have (E)- or (Z)-configuration. Hence, 1-(2,6,6-trimethylcyclohex-2-en-1-yl)but-2-en-1-one (α-damascone) can be present in the form either of (E,1R)-1-(2,6,6-trimethylcyclohex-2-en-1-yl)but-2-en-1-one, (E,1S)-1-(2,6,6-trimethylcyclohex-2-en-1-yl) but-2-en-1-one, (Z,1R)-1-(2,6,6-trimethylcyclohex-2-en-1-yl)but-2-en-1-one or (Z,1S)-1-(2,6,6-trimethylcyclohex-2-en-1-yl)but-2-en-1-one, respectively, hereinafter termed the (E,1R)-isomer, the (E,1S)-isomer, the (Z,1R)-isomer or the (Z,1S)-isomer, or in the form of mixtures of these isomers, hereinafter termed (E/Z,1R/1S)-isomer mixtures.

The term "1-(2,6,6-trimethylcyclohex-2-en-1-yl)but-2-en-1-one" thus encompasses the pure (E,1R)-isomer, (E,1S)-isomer, (Z,1R)-isomer and (Z,1S)-isomer, as well as mixtures, where these isomers are present in equal amounts or wherein one or two of these isomers are present in excess.

Frequently, the present process provides 1-(2,6,6-trimethylcyclohex-2-en-1-yl)but-2-en-1-one as pure (E,1R)-isomer or pure (E,1S)-isomer or as mixtures, where these two isomers are present in equal amounts or wherein one of these isomers is present in excess.

More frequently, the present process provides 1-(2,6,6-trimethylcyclohex-2-en-1-yl)but-2-en-1-one as (E,1R/1S)-isomer mixtures, where these two isomers are present in equal amounts or wherein one of these isomers is present in excess.

Similarly, the double bond between C5 and C6 of the intermediate 6,10-dimethylundeca-1,5,9-trien-4-ol may have (E)- or (Z)-configuration. Hence, 6,10-dimethylundeca-1,5,9-trien-4-ol can be present in the form either of (5E)-6,10-dimethylundeca-1,5,9-trien-4-ol or (5Z)-6,10-dimethylundeca-1,5,9-trien-4-ol or in the form of mixtures of these isomers.

The term "6,10-dimethylundeca-1,5,9-trien-4-ol" thus encompasses both the pure (5E)-isomer and (5Z)-isomer, as well as mixtures, where these two isomers are present in equal amounts or wherein one of these isomers is present in excess.

Likewise, the double bond between C5 and C6 of the intermediate 6,10-dimethylundeca-1,5,9-trien-4-one may have (E)- or (Z)-configuration. Hence, 6,10-dimethylundeca-1,5,9-trien-4-one can be present in the form either of (5E)-6,10-dimethylundeca-1,5,9-trien-4-one or (5Z)-6,10-dimethylundeca-1,5,9-trien-4-one or in the form of mixtures of these isomers.

The term "6,10-dimethylundeca-1,5,9-trien-4-one" thus encompasses both the pure (5E)-isomer and pure (5Z)-isomer, as well as mixtures, where these two isomers are present in equal amounts or wherein one of these isomers is present in excess.

Step a):

According to the present invention, step a) comprises the preparation of 6,10-dimethylundeca-1,5,9-trien-4-ol. 6,10-dimethylundeca-1,5,9-trien-4-ol can, by way of example, be obtained in a convenient way from 3,7-dimethylocta-2,6-dienal (citral) by reacting 3,7-dimethylocta-2,6-dienal with an allylmagnesium compound, as well as by other processes that are known to the skilled person and that are well described in the prior art.

In a preferred embodiment of the present process, the 6,10-dimethylundeca-1,5,9-trien-4-ol provided in step a) is prepared by reacting 3,7-dimethylocta-2,6-dienal (citral) with an allylmagnesium compound.

The starting material 3,7-dimethylocta-2,6-dienal can either be purchased as pure (6E)-3,7-dimethylocta-2,6-dienal (geranial) and pure (6Z)-3,7-dimethylocta-2,6-dienal (neral) or as a mixture of (6E)-3,7-dimethylocta-2,6-dienal (geranial) and (6Z)-3,7-dimethylocta-2,6-dienal (neral) or can be prepared using processes that are known to the skilled person. Pure geranial and pure neral as well as mixtures thereof, are equally suitable as starting material for the preparation of 6,10-dimethylundeca-1,5,9-trien-4-ol in step a) of the present process.

Generally, all common allylmagnesium compounds known to the skilled person can be applied in the transformation of 3,7-dimethylocta-2,6-dienal to 6,10-dimethylundeca-1,5,9-trien-4-ol.

Suitable allylmagnesium compounds are for example allylmagnesium halides, such as allylmagnesium chloride or allylmagnesium bromide.

Preferably, the allylmagnesium compounds are selected from allylmagnesium chloride or allylmagnesium bromide, in particular allylmagnesium chloride.

Typically, the allylmagnesium compound is used in an amount of from 0.95 to 1.5 equivalents, preferably in an amount of from 1.0 to 1.4 equivalents, in particular in an amount of from 1.0 to 1.3 equivalents, based on the total amount of 3,7-dimethylocta-2,6-dienal in the reaction mixture.

The transformation can be carried out in the temperature range of from −20 to 50° C., preferably in the range of from −15 to 30° C., in particular in the range of from −10 to 15° C.

Preferably, the transformation is carried out at ambient pressure.

The transformation may be carried out in the presence or the absence of an organic solvent.

Preferably, the transformation is carried out in the presence of an inert organic solvent.

The expression "inert organic solvent" generally means an organic solvent, which under the prevailing reaction conditions does not enter into any reactions with the starting materials or reagents participating in the reaction, or with the resultant products.

Suitable inert organic solvents include, but are not limited to the following groups:

group S1: aliphatic and alicyclic hydrocarbons, in particular alkanes and cycloalkanes having 5 to 12 carbon atoms and mixtures of these alkanes and cycloalkanes, such as pentane, hexane, heptane, octane, ligroin, petrol ether or cyclohexane;

group S2: aromatic hydrocarbons, such as benzene, toluene, xylenes, ethylbenzene or tetralin, and mixtures thereof;

group S3: aliphatic and alicyclic ethers, such as methyl-tert.-butylether, dibutyl ether, tetrahydrofurane, 1,4-dioxane or 1,2-dimethoxyethane;

as well as mixtures of the aforementioned solvents.

More preferably, the transformation is carried out in an inert organic solvent selected from solvents of the group S2 and S3, in particular THF, diethyl ether or toluene.

After the transformation has finished, the reaction mixture is typically subjected to extractive work-up. Generally, the crude 6,10-dimethylundeca-1,5,9-trien-4-ol is obtained in high yields, i.e. in a yield of at least 90%, frequently in a yield of at least 95% or more, for example in a yield of 98% or 99%. Hence, additional purification of the thus obtained crude 6,10-dimethylundeca-1,5,9-trien-4-ol is usually not required.

Generally, the E/Z-isomer ratio of the obtained 6,10-dimethylundeca-1,5,9-trien-4-ol is determined by the E/Z-isomer ratio of the starting material, e.g. 3,7-dimethylocta-2,6-dienal. An isomerization is typically not observed or only observed to a minor extend during the process of the present invention. For example, if pure (6E)-3,7-dimethyl-octa-2,6-dienal (geranial) is used as the starting material the 6,10-dimethylundeca-1,5,9-trien-4-ol is obtained as pure (5E)-isomer, or at least as an (5E)/(5Z)-isomer mixture, where the (5E)-isomer is present in an large excess.

Step b):

Step b) of the present invention comprises the oxidation of 6,10-dimethylundeca-1,5,9-trien-4-ol provided in step a) with an oxidizing agent in the presence of at least one organic nitroxyl radical, at least one nitrate compound and an inorganic solid to yield 6,10-dimethylundeca-1,5,9-trien-4-one.

Suitable organic nitroxyl radicals are typically selected from stable organic nitroxyl radicals.

Preferably, the organic nitroxyl radicals used in step b) of the present invention are selected from (2,2,6,6-tetramethylpiperidin-1-yl)oxyl compounds, 2-azaadamantane N-oxyl compounds, (1,1,3,3-tetramethylisoindolin-2-yl)oxyl compounds, 9-azanoradamantane N-oxyl, 9-azabicyclo[3.3.1] nonane-N-oxyl, 2,2,5-trimethyl-4-phenyl-3-azahexane-3-nitroxide, diphenylnitroxyl, di-tert.-butylnitroxyl and mixtures thereof.

Preferred (2,2,6,6-tetramethylpiperidin-1-yl)oxyl compounds are for example (2,2,6,6-tetramethylpiperidin-1-yl)oxyl (TEMPO), 4-hydroxy-(2,2,6,6-tetramethylpiperidin-1-yl)oxyl (4-hydroxy TEMPO), 4-acetamido-(2,2,6,6-tetramethylpiperidin-1-yl)oxyl (4-acetamido TEMPO) or 4-amino-(2,2,6,6-tetramethylpiperidin-1-yl)oxyl (4-amino TEMPO).

Preferred 2-azaadamantane-N-oxyl compounds are for example 2-azaadamantane-N-oxyl (AZADO), 1-methyl-2-azaadamantane-N-oxyl (1-methyl AZADO), 5-fluoro-2-azaadamantane-N-oxyl or 1-fluoro-2-azaadamantane-N-oxyl.

Preferred (1,1,3,3-tetramethylisoindolin-2-yl)oxyl compounds are for example (1,1,3,3-tetramethylisoindolin-2-yl)oxyl (TMIO), 5-amino-(1,1,3,3-tetramethylisoindolin-2-yl)oxyl or 5-nitro-(1,1,3,3-tetramethylisoindolin-2-yl)oxyl.

More preferably, the organic nitroxyl radicals used in step b) of the present invention are selected from (2,2,6,6-tetramethylpiperidin-1-yl)oxyl compounds and 2-azaadamantane N-oxyl compounds as well as mixtures thereof.

In particular, the organic nitroxyl radicals used in step b) of the present invention are selected from (2,2,6,6-tetramethylpiperidin-1-yl)oxyl compounds, especially from (2,2,6,6-tetramethylpiperidin-1-yl)oxyl (TEMPO) and 4-hydroxy-(2,2,6,6-tetramethylpiperidin-1-yl)oxyl (4-hydroxy TEMPO).

Preferably, the total amount of the at least one nitroxyl radical used in step b) is in the range of 1 to 50 mol-%, more preferably in the range of 3 to 40 mol-%, in particular in the range of 5 to 30 mol-%, based on the amount of 6,10-dimethylundeca-1,5,9-trien-4-ol in the reaction mixture.

Typically, the nitrate compound used in step b) of the present process is selected from nitrate salts, for example alkali metal nitrates, earth alkaline metal nitrates, transition metal nitrates or ammonium nitrate, and nitric acid ($HNO_3$) as well as mixtures thereof.

For the purpose of the present invention the metal nitrates mentioned before and below do not only relate to the pure metal nitrates but also include their hydrated form(s).

Preferably, the nitrate compound used in step b) of the present process is selected from transition metal nitrates and nitric acid ($HNO_3$) as well as mixtures thereof. Preferred transition metal nitrates are for example iron(III) nitrate or copper(II) nitrate.

More preferably, the nitrate compound used in step b) of the present process is selected from iron(III) nitrate and nitric acid ($HNO_3$).

In a particularly preferred embodiment of the present invention, the nitrate compound used in step b) of the present process is iron(III) nitrate.

In yet another particularly preferred embodiment of the present invention, the nitrate compound used in step b) of the present process is nitric acid ($HNO_3$).

Preferably, the total amount of the at least one nitrate compound used in step b) is in the range of 1 to 50 mol-%, more preferably in the range of 3 to 40 mol-%, in particular in the range of 5 to 30 mol-%, based on the amount of 6,10-dimethylundeca-1,5,9-trien-4-ol in the reaction mixture.

Preferably, the molar ratio of the at least one nitroxyl radical to the at least one nitrate compound used in step b) of the present invention is in the range of 1:10 to 10:1, more preferably in the range of 1:5 to 5:1, in particular in the range of 1:2 to 2:1.

Generally, the oxidation in step b) is performed in the presence of an inorganic solid.

Preferably, the inorganic solid is selected from metal oxides, metal carbonates, metal sulfates, metal halides, ammonium carbonate, ammonium sulfate or ammonium halides.

Even more preferred, the inorganic solid is selected from alkali metal halides, such as LiF, LiCl, LiBr, LiI, KF, KCl, KBr, KI, NaF, NaCl, NaBr, NaI, RbF, RbCl, RbBr, RbI, CsF, CsCl, Cs Br or CsI and alkali earth metal halides, such as $BeF_2$, $BeCl_2$, $MgF_2$, $MgCl_2$, $CaF_2$, $CaCl_2$, $SrF_2$, $SrCl_2$, $BaF_2$ or $BaCl_2$. Even more preferred, the inorganic solid is selected from alkali metal chlorides and alkali earth metal chlorides, In particular, the inorganic solid is selected from LiF, LiCl, KF, KCl, NaF and NaCl and mixtures thereof. Especially, the inorganic solid is NaCl or LiCl or a mixture thereof.

Preferably, the inorganic solid used in the oxidation in step b) of the present process is applied in the form of solid particles, e.g. in the form of small granules. The particle size of the solid particles is of minor importance and may range e.g. from 10 µm to 5 mm, especially from 50 µm to 2 mm (D [4.3] value as determined e.g. by light scattering).

Preferably, the total amount of the inorganic solid used in step b) of the present process is in the range of 0.5 to 20% by weight, more preferably in the range of 1 to 15% by weight, in particular in the range of 2 to 10% by weight, based on the amount of 6,10-dimethylundeca-1,5,9-trien-4-ol in the reaction mixture.

Preferably, the molar ratio of the at least one nitroxyl radical to the inorganic solid used 35 in step b) of the present invention is in the range of 1:10 to 10:1, more preferably in the range of 1:5 to 5:1, in particular in the range of 1:2 to 2:1.

In principal, any oxidizing agent that is capable of oxidizing organic nitroxyl radicals or the N-hydroxy form thereof, respectively, to the corresponding highly electrophilic oxoammonium species, which is believed to be the active oxidizing species that reacts with the substrate alcohols, can be used as oxidizing agent in step b) of the present process.

Suitable oxidizing agents are by way of example selected from halogens, oxygen, oxyanions of chlorine, oxyanions of bromine, oxyanions of iodine, dialkyl peroxides, organic and inorganic peroxy acids, peresters, hydroperoxides and hydrogen peroxide.

Suitable halogens are by way of example fluorine or chlorine.

Suitable oxyanions of chlorine are by way of example hypochlorites, chlorites, chlorates or perchlorates.

Suitable oxyanions of bromine are by way of example hypobromites, bromites, bromates or perbromates.

Suitable oxyanions of iodine are by way of example hypoiodites, iodites, iodates or periodates.

Suitable dialkyl peroxides are by way of example diisopropyl peroxide or di(tert.-butyl) peroxide.

Suitable organic or inorganic peroxy acids are for example, meta-chloroperoxybenzoic acid or peracetic acid, peroxydisulfuric acid or peroxymonosulphuric acid.

Suitable peresters are by way of example peracetates, such as tert.-butyl peracetate or tert.-butyl phenylperacetate.

A suitable hydroperoxide is by way of example a tert.-butyl hydroperoxide.

For the purpose of the present invention, the expressions "hypochlorites", "chlorites", "chlorates" or "perchlorates" relate to any salt containing the oxyanion $ClO^-$ (hypochlorite), $ClO_2^-$ (chlorite), $ClO_3^-$ (chlorate) or $ClO_4^-$ (perchlorate), respectively, e.g. the alkali or earth alkali metal salts thereof.

For the purpose of the present invention, the expressions "hypobromites", "bromites", "bromates" or "perbromates" relate to any salt containing the oxyanion $BrO^-$ (hypobromite), $ClO_2^-$ (bromite), $ClO_3^-$ (bromate) or $ClO_4^-$ (perbromate), respectively, e.g. the alkali or earth alkali metal salts thereof.

For the purpose of the present invention, the expressions "hypoiodites", "iodites", "iodates" or "periodates" relate to any salt containing the oxyanion $IO^-$ (hypoiodite), $IO_2^-$ (iodite), $IO_3^-$ (iodate) or $IO_4^-/IO_6^{5-}$ (periodate), respectively, e.g. the alkali or earth alkali metal salts thereof.

Preferably, the oxidizing agent used in step b) of the present invention is selected from hypochlorites, hydrogen peroxide and molecular oxygen, in particular from molecular oxygen, hereinafter also termed oxygen.

In a particular preferred embodiment of the present invention, the oxidation reaction in step b) of the present invention is performed under oxygen atmosphere.

The molecular oxygen can be applied to the reaction system at the start of the oxidation reaction or over the whole course of the oxidation reaction. The oxygen pressure in the reaction system may thereby be held close to atmospheric pressure or may be set to a pressure above atmospheric pressure, e.g. to a pressure in the range of 1.1 to 10 bar.

In a preferred embodiment of the present invention, the oxygen is introduced to the oxidation reaction in step b) in the form of an oxygen stream.

The oxygen stream can be passed into the gas space of the reaction system or into the liquid reaction mixture. The introduction of the oxygen stream into the reaction system preferably takes place in a manner that creates a large area for interchange between the liquid reaction mixture and the oxygen gas.

It is preferred, that the oxygen stream is introduced into the reaction mixture below the liquid surface in such a way that it bubbles through the reaction mixture. The oxygen stream can be fed into the system by way of any desired suitable apparatuses. Among these are by way of example nozzles for gas-supply lances. The nozzles can be on the base of the reactor or in the vicinity of the base. There can also be a plurality of nozzles e.g. arranged in the form of a ring.

It is preferable that the reaction mixture is mixed in order to bring about an interchange of reaction mixture in the reactor region below the feed of the oxygen stream with reaction mixture in the reactor region above the feed of the oxygen stream. By way of example, stirrers or a circulating pump are suitable for the mixing process. In one specific variant, what is known as a gas-introducing stirrer is used for the introduction of the oxygen stream and for the mixing of the reaction mixture.

Generally, the oxidizing agent used in step b) of the present process is applied in excess, based on the amount of 6,10-dimethylundeca-1,5,9-trien-4-ol in the reaction mixture.

More specifically, the oxidizing agent used in step b) is applied in an amount of at least 2 mol, preferably of at least 3 mol, in particular of at least 5 mol, per 1 mol of 6,10-dimethylundeca-1,5,9-trien-4-ol present in the reaction mixture, whereby the molar amount of the specified oxidizing-agent above is calculated as oxygen equivalents.

For the purposes of the present invention, the term "oxygen equivalent" relates to the number of oxygen atoms that can be released by a given oxidant. For example, inorganic or organic peroxy acids as well as $H_2O_2$ can release one oxygen atom. Hypochlorite ($ClO^-$) can also release one oxygen atom, while chlorite ($ClO_2^-$) can typically release two oxygen atoms.

The oxidation reaction is typically carried out in the presence of an organic solvent or an organic solvent mixture.

It is preferred that the oxidation reaction is carried out in the presence of an organic solvent, which is inert under the reaction conditions. Preferred inert organic solvents include, but are not limited to the following groups:

group S1: aliphatic and alicyclic hydrocarbons, in particular alkanes and cycloalkanes having 5 to 12 carbon atoms and mixtures of these alkanes and cycloalkanes, such as pentane, hexane, heptane, octane, ligroin, petrol ether or cyclohexane;

group S2: aromatic hydrocarbons, such as benzene, toluene, xylenes, ethylbenzene or tetralin, and mixtures thereof;

group S3: aliphatic and alicyclic ethers, such as methyl-tert.-butylether, dibutyl ether, tetrahydrofurane, 1,4-dioxane or 1,2-dimethoxyethane;

group S4: halogenated aliphatic hydrocarbons, such as dichloromethane, trichloromethane, tetrachloromethane or dichloroethane, and mixtures thereof;

group S5: halogenated aromatic hydrocarbons, such as chlorobenzene, dichlorobenzene, 2-chlortoluene, 3-chlortoluene or 4-chlorotoluene, and mixtures thereof;

as well as mixtures of the aforementioned solvents.

More preferably, the oxidation is carried out in an inert organic solvent selected from solvents of the groups S2 and S4, in particular toluene or dichloromethane.

Typically, the oxidation reaction is performed at a temperature in the range of 0° C. to 100° C., preferably in the range of 5 to 70° C., in particular in the range of 10 to 50° C.

The chlorination reaction is typically performed at ambient pressure or at reduced or elevated pressure. It is preferable that the chlorination reaction is carried out at ambient or elevated pressure.

The oxidation reaction can take place in the absence of or in the presence of an inert gas. The expression inert gas generally means a gas which under the prevailing reaction conditions does not enter into any reactions with the starting materials, reagents, or solvents participating in the reaction, or with the resultant products. Examples of inert gases are $N_2$, $CO_2$ and noble gases like He, Ne, Ar, Kr and Xe. If the oxidation reaction is performed in the presence of an inert gas, the inert gas is preferably selected from $N_2$ or Ar. Preferably, the oxidation reaction is performed in the absence of an inert gas, in particular if oxygen is used as the oxidizing agent.

It has been found beneficial, if the at least one organic nitroxyl radical, the at least one nitrate compound and the inorganic solid are applied in about equal molar amounts in the oxidation reaction in step b) of the present process.

In a preferred embodiment of the present invention the at least one organic nitroxyl radical (A), the at least one nitrate compound (B) and the inorganic solid (C) are applied in a molar ratio (A:B:C) of 1:(0.7-1.3):(0.7-1.3), more preferably of 1:(0.8-1.2):(0.8-1.2), in particular of 1:(0.9-1.1):(0.9-1.1), in the oxidation reaction in step b) of the present process.

It is further preferred that the at least one nitroxyl radical, the at least one nitrate compound and the inorganic solid are added to 6,10-dimethylundeca-1,5,9-trien-4-ol provided in step a).

The at least one nitroxyl radical, the at least one nitrate compound and the inorganic solid are hereinafter also termed "the catalyst mixture".

The catalyst mixture can be added at the start of the oxidation reaction or over the course of the oxidation reaction. The expression "course of the reaction" relates to the time interval between the start of the oxidation reaction, i.e. when the oxidizing agent and 6,10-dimethylundeca-1,5,9-trien-4-ol provided in step a) are brought together and the reaction parameters are such that the oxidation reaction can take place, and the end of the reaction, i.e. when the 6,10-dimethylundeca-1,5,9-trien-4-ol is consumed and/or no further 6,10-dimethylundeca-1,5,9-trien-4-one is formed. It is preferred that the catalyst mixture is added over the course of the reaction. Thereby, it is achieved that a steady amount of active catalyst mixture is present in the reaction mixture.

Adding the catalyst mixture over the course of the reaction is beneficial with regard to clean and rapid conversion.

The catalyst mixture can be added to the 6,10-dimethylundeca-1,5,9-trien-4-ol provided in step a) in one or more portions or continuously with constant or changing addition rates. Preferably, the catalyst mixture is added in several portions, e.g. in 2 to 20 portions, or continuously, preferably with constant addition rates, to the 6,10-dimethylundeca-1,5,9-trien-4-ol provided in step a).

It was found beneficial, if the catalyst mixture is added in two or more portions, e.g. in defined amounts in regular time intervals, for example every 1 to 5 hours, e.g. every 2 or 3 hours, or continuously with constant addition rates to the 6,10-dimethylundeca-1,5,9-trien-4-ol provided in step a), until all the 6,10-dimethylundeca-1,5,9-trien-4-ol is consumed.

Typically, the reaction time is in the range of 2 to 12 hours, often in the range of 3 to 8 hours.

After the oxidation reaction has finished, the reaction mixture is typically filtered to remove inorganic materials and subjected to extractive work-up. The thus obtained crude 6,10-dimethylundeca-1,5,9-trien-4-one is then, by way of example, purified by using chromatographic purification methods, such as column chromatography, or by distillation.

Suitable distillation devices for the purification of 6,10-dimethylundeca-1,5,9-trien-4-one are for example distillation columns, such as tray columns optionally equipped with bubble cap trays, sieve plates, sieve trays, packages or filler materials, or spinning band columns, such as thin film evaporators, falling film evaporators, forced circulation evaporators, Sambay evaporators, etc. and combinations thereof.

The oxidation reaction in step b) of process of the invention can be designed to take place either continuously or batchwise. The batchwise oxidation can be conducted in a reaction apparatus conventionally used for this purpose, e.g. a stirred reactor, which is optionally equipped with metering devices. Step b) of the process of the present invention may also be carried out continuously, e.g. in a tube reactor or in a cascade of at least two stirred reactors, which may be back-mixed or not.

Step c)

Step c) of the present invention comprises the reaction of the 6,10-dimethylundeca-1,5,9-trien-4-one obtained in step b) with an acid to yield 1-(2,6,6-trimethylcyclohex-2-en-1-yl)but-2-en-1-one.

This reaction involves the cyclization of 6,10-dimethylundeca-1,5,9-trien-4-one to 1-(2,6,6-trimethylcyclohex-2-en-1-yl)but-3-en-1-one as well as the rearrangement of the terminal double bond of the 3-butenoyl group of 1-(2,6,6-trimethylcyclohex-2-en-1-yl)but-3-en-1-one to 1-(2,6,6-trimethylcyclohex-2-en-1-yl)but-2-en-1-one. Both reactions, i.e. the cyclization reaction and the rearrangement reaction, proceed at the same time.

Suitable acids that can be used in step c) of the present process are preferably selected from Lewis-acids and Brønsted-acids. Preferred Lewis acids are by way of example $BF_3$, such as $BF_3$ diethyl etherate, $TiCl_4$, $AlCl_3$, $FeCl_3$, $SbCl_3$, $SbCl_5$, $TiCl_4$, $ZnCl_2$ or $ZnBr_2$. Preferred Brønsted-acids are by way of example selected from mineral acids, such as $H_2SO_4$, polyphosphoric acid, $H_3PO_4$ or $HClO_4$, sulfonic acids, such as p-toluenesulfonic acid, methanesulfonic acid or trifluoromethanesulfonic acid, formic acid and trifluoroacetic acid.

More preferable, the acid used in step c) of the present process is selected from mineral acids, even more preferably from $H_2SO_4$ or $H_3PO_4$, in particular from $H_3PO_4$.

Preferably, the total amount of the acid used in step c) of the present process is in the range of 0.9 to 5 mol, more preferably in the range of 1.0 to 4 mol, in particular in the range of 1.1 to 3 mol, per 1 mol of 6,10-dimethylundeca-1,5,9-trien-4-one.

Step c) of the present process is preferably carried out in the presence of an inert organic solvent selected from nitroalkanes, such as nitromethane, nitroethane, 1-nitropropane, 2-nitropropane or 1-nitrobutane, and solvents of the groups S1 to S5, as defined above, as well as mixtures thereof.

It is further preferred, that the inert organic solvent used in the reaction of step c) of the present process has a boiling point at 1013 mbar of at least 70° C., more preferably of at least 80° C.

More preferably, step c) of the present process is carried out in the presence of an inert organic solvent selected from nitroalkanes and solvents of the groups S2 and S5, as defined above, having a boiling point at 1013 mbar of at least 80° C. In particular step c) of the present process is carried out in the presence of nitromethane, benzene or toluene.

Typically, the reaction in step c) of the present process is performed at a temperature in the range of 20° C. to 150° C., preferably in the range of 40 to 130° C., in particular in the range of 60 to 110° C.

The reaction in step c) of the present process may be performed at ambient pressure or at reduced or elevated pressure, preferable at ambient or elevated pressure, in particular at ambient pressure.

The reaction in step c) of the present process can take place in the absence of or in the presence of an inert gas, as defined above. If the reaction is performed in the presence of an inert gas, the inert gas is preferably selected from $N_2$ or Ar. Preferably, the reaction in step c) of the present invention is performed in the absence of an inert gas.

After completion of the cyclization/isomerization reaction, the reaction mixture is quenched by the addition of water and/or an aqueous alkaline solution and subjected to extractive work-up. The thus obtained crude 1-(2,6,6-trimethylcyclohex-2-en-1-yl)but-2-en-1-one is then subjected to conventional purification measures, including distillation or chromatography or combined measures. Preferably, the crude 1-(2,6,6-trimethylcyclohex-2-en-1-yl)but-2-en-1-one obtained in step c) of the present process is purified using chromatographic purification methods, such as column chromatography.

The 1-(2,6,6-trimethylcyclohex-2-en-1-yl)but-2-en-1-one can generally be obtained in a purity of at least 80%, e.g. in a purity of 90%, as (E/Z,1R/1S)-isomer mixtures or (E,1R/1S)-isomer mixtures, respectively, as defined above.

In principle, the (1R/1S)-isomer composition of 1-(2,6,6-trimethylcyclohex-2-en-1-yl)but-2-en-1-one may be influenced by the isomer composition of the starting material 6,10-dimethylundeca-1,5,9-trien-4-one, i.e. the (E/Z)-ratio of the double bond between C5 and C6, the type of acid used, the reaction temperature and/or the solvent used for the cyclization reaction. However, the (E/Z)-ratio of the starting material 6,10-dimethylundeca-1,5,9-trien-4-one is not critical for the cyclization/isomerization reaction of the present process.

It was surprisingly found that the cyclization reaction in step c) typically includes the rearrangement of the terminal double bond of the 3-butenoyl group of 1-(2,6,6-trimethylcyclohex-2-en-1-yl)but-3-en-1-one to the 2-butenoyl group (crotonyl group) of 1-(2,6,6-trimethylcyclohex-2-en-1-yl)but-2-en-1-one (α-damascone). The non rearranged cyclization product 1-(2,6,6-trimethylcyclohex-2-en-1-yl)but-3-en-1-one could only be observed to a minor extend.

More specifically, the product mixture obtained in step c) of the present invention comprises less than 15% by weight, preferably less than 10% by weight, in particular less than 5% by weight, for example 4 or 2% by weight, of 1-(2,6,6-trimethylcyclohex-2-en-1-yl)but-3-en-1-one, based on the total amount of 1-(2,6,6-trimethylcyclohex-2-en-1-yl)-but-3-en-1-one and 1-(2,6,6-trimethylcyclohex-2-en-1-yl)but-2-en-1-one in the product mixture.

The double bond of the 2-butenoyl group of 1-(2,6,6-trimethylcyclohex-2-en-1-yl)but-2-en-1-one, obtained after the cyclization/rearrangement reaction in step c) of the present process, may have (E)- or (Z)-configuration. Under the prevailing reaction conditions of step c) of the present process, the 1-(2,6,6-trimethylcyclohex-2-en-1-yl)but-2-en-1-one is often obtained as (E/Z)-isomer mixture, where the (E)-isomer is present in excess, e.g. to at least 60% or 75%, based on the total amount of the (E)- and (Z)-isomer of 1-(2,6,6-trimethylcyclohex-2-en-1-yl)but-2-en-1-one present in the product mixture.

The cyclization and in-situ isomerization reaction in step c) of the present process can be designed to take place either continuously or batchwise. The batchwise cyclization and in-situ isomerization can be conducted in a reaction apparatus conventionally used for this purpose, e.g. a stirred reactor, which is optionally equipped with metering devices. Step c) of the present process may also be carried out continuously, e.g. in a tube reactor or in a cascade of at least two stirred reactors, which may be back-mixed or not.

Isomerization Step:

If desired, the proportion of 1-(2,6,6-trimethylcyclohex-2-en-1-yl)but-2-en-1-one in the product mixture may be further increased by subjecting the 1-(2,6,6-trimethylcyclohex-2-en-1-yl)but-2-en-1-one obtained in step c) of the present invention, comprising minor amounts of 1-(2,6,6-trimethylcyclohex-2-en-1-yl)but-3-en-1-one, to an additional isomerization step.

The isomerization of the residual 1-(2,6,6-trimethylcyclohex-2-en-1-yl)but-3-en-1-one to 1-(2,6,6-trimethylcyclohex-2-en-1-yl)but-2-en-1-one (α-damascone) can be achieved by adding a base or an acid, preferably an acid, to the product mixture obtained in step c) of the present process.

Suitable bases that may be applied in this optional isomerization reaction are selected from alkaline metal and earth alkaline metal hydroxides or alkaline metal and earth alkaline metal alcoholates. Suitable alkaline metal and earth alkaline metal alcoholates are by way of example potassium ethanolate, sodium ethanolate, potassium isopropanolate, sodium isopropanolate, potassium tert.-butanolate or sodium tert.-butanolate. Particularly suitable bases are potassium tert.-butanolate or sodium tert.-butanolate.

Preferred acids that can be applied in the optional isomerization reaction are selected from Brønsted-acids, as defined above. Mineral acids are preferably applied in the form of aqueous solutions.

The isomerization reaction is preferably performed in the presence of an organic solvent selected from alkanols, such as ethanol, isopropanol or tert.-butanol, nitroalkanes or solvents of the groups S2 and S5, as defined above.

The optional isomerization reaction is preferably performed at a temperature in the range of 30 to 150° C., in particular in the range of 50 to 120° C.

After completion of the optional isomerization reaction, the reaction mixture is quenched by the addition of water and/or an aqueous acidic or basic solution, respectively, and subjected to extractive work-up. The thus obtained crude 1-(2,6,6-trimethylcyclohex-2-en-1-yl)but-2-en-1-one is then subjected to conventional purification measures, including distillation or chromatography or combined measures, as described above.

EXAMPLES

Example 1

Synthesis of 6,10-dimethylundeca-1,5,9-trien-4-ol from citral (step a)

To a stirred solution of citral (100 g, 0.65 mol) in dry THF (750 ml) was added allyl magnesium chloride (362.6 ml, 2M in THF, 0.72 mol) dropwise while maintaining the temperature between 0° C. to 5° C. After complete addition of allylmagnesium chloride reaction mixture was stirred for one hour at 0° C. and the progress of the reaction was monitored by TLC. After completion of reaction the mixture was quenched by adding saturated ammonium chloride solution (500 ml) at 0-10° C. The aqueous layer was extracted by ethyl acetate (3×50 ml) and the combined organic layer was concentrated to afford 127 g of compound 2 (99.5%).

$^1$HNMR (300 MHz, CDCl$_3$) δ 1.53 (s, 3H), 1.61 (s, 6H), 1.94-2.07 (m, 4H), 2.18-2.23 (m, 2H), 4.34-4.36 (m, 1H), 5.01-5.14 (m, 4H), 7.72-5.75 (m, 1H).

Example 2

Synthesis of 6,10-dimethylundeca-1,5,9-trien-4-one using TEMPO/Iron(III) nitrate nonahydrate/NaCl (step b)

Iron(III) nitrate nonahydrate (2.0 g, 5.1 mmol, 0.1 eq), TEMPO (0.79 g, 5.1 mmol, 0.1 eq) and solid NaCl (0.29 g, 51 mmol, 0.1 eq) was added to 50 ml of toluene at 25° C. To this mixture, the 6,10-dimethylundeca-1,5,9-trien-4-one obtained in example 1 (10.0 g, 51 mmol, 1 eq) was added at 25° C. and was stirred for 3 hours under oxygen atmosphere (O$_2$ gas was continuously passed through the reaction mixture). The reaction was monitored by TLC and HPLC, which showed 50% conversion. After 3 hours of stirring an additional amount if Iron(III) nitrate nonahydrate (2.0 g, 5.1 mmol, 0.1 eq), TEMPO (0.79 g, 5.1 mmol, 0.1 eq), NaCl (0.29 g, 5.1 mmol, 0.1 eq) was added again to reaction mixture at 25° C. and the reaction mixture was then stirred for additional 2 hours. After consumption of almost 95% starting material (based on TLC and HPLC), the reaction mixture was diluted by adding toluene (20 ml). Reaction mixture was filtered to remove inorganic materials and the filtrate was washed by saturated sodium thiosulfate solution (150 ml), 1N HCl (150 ml), saturated sodium bicarbonate solution (150 ml), brine (150 ml). The combined organic layer was dried over sodium sulfate and concentrated to afford 13.0 g of crude compound which was purified by column chromatography. The yield of purified compound was 72%, based on the starting material. For other batches crude compound was purified by distillation.

$^1$HNMR (300 MHz, CDCl$_3$) (Mixture of E and Z isomers) δ 1.63 (s, 3H), 1.68 (s, 3H), 1.9 (s, 1H), 2.07-2.09 (m,4H), 2.50-2.55 (m, 0.5H), 3.09-3.14 (m,1.5H), 5.0-5.23 (m, 3H), 5.84-5.93 (m, 1H), 6.01 (bs, 1H).

Example 3

Synthesis of 6,10-dimethylundeca-1,5,9-trien-4-one using 4-OH TEMPO/Iron(III) nitrate nonahydrate/NaCl (step b)

Iron(III) nitrate nonahydrate (13.3 g, 32.9 mmol, 0.1 eq), 4-Hydroxy TEMPO (5.7 g, 32.9 mmol, 0.1 eq) and solid NaCl (1.9 g, 32.9 mmol, 0.1 eq) was added to 350.0 ml of toluene at 25° C. To this mixture, the 6,10-dimethylundeca-1,5,9-trien-4-ol obtained in example 1 (64.0 g, 329.8 mmol, 1 eq) was added and stirred for 3 hours at 45° C. under oxygen atmosphere (O$_2$ gas was continuously passed through the reaction mixture). The reaction was monitored by TLC and HPLC, which showed 50% conversion. After 3 hours of stirring, an additional amount if Iron(III) nitrate nonahydrate (13.3 g, 32.9 mmol, 0.1 eq), 4-Hydroxy TEMPO (5.7 g, 32.9 mmol, 0.1 eq) and NaCl (1.9 g, 32.9 mmol, 0.1 eq) was added again to reaction mixture at 45° C. and the reaction mixture was then stirred for additional 2 hours. After consumption of almost 95% starting material (based on TLC and HPLC), the reaction mixture was diluted by adding toluene (100.0 ml). Reaction mixture was filtered to remove inorganic materials and the filtrate was washed by saturated sodium thiosulfate solution (250.0 ml), 1N HCl (250.0 ml), saturated sodium bicarbonate solution (300.0 ml), brine (250.0 ml). The combined organic layer was dried over sodium sulfate and concentrated to afford 61.0 g of crude compound which was purified by vacuum distillation at 80° C./1.8 mbar to get 30.0 g (Yield: 50%) product.

$^1$HNMR (300 MHz, CDCl$_3$) (Mixture of E and Z isomers) δ 1.63 (s, 3H), 1.68 (s, 3H), 1.9 (s, 1H), 2.07-2.09 (m,4H), 2.50-2.55 (m, 0.5H), 3.09-3.14 (m,1.5H), 5.0-5.23 (m, 3H), 5.84-5.93 (m, 1H), 6.01 (bs, 1H).

Example 4

Synthesis of 6,10-dimethylundeca-1,5,9-trien-4-one using TEMPO/Iron(III) nitrate nonahydrate/LiCl (step b)

The process of example 2 was repeated using same molar amount of LiCl instead of NaCl. The conversion of the starting material was 90%. After purification by column chromatography 6,10-dimethylundeca-1,5,9-trien-4-one was obtained with 70% yield.

Example 5

Synthesis of 6,10-dimethylundeca-1,5,9-trien-4-one using TEMPO/Iron(III) nitrate nonahydrate/KCl (step b)

The process of example 2 was repeated using same molar amount of KCl instead of NaCl. The conversion of the starting material was 50%. After purification by column chromatography 6,10-dimethylundeca-1,5,9-trien-4-one was obtained with 35% yield.

Example 6

Synthesis of 6,10-dimethylundeca-1,5,9-trien-4-one using HNO$_3$/4-OH TEMPO (step b)

Nitric acid (70%) (0.22 g, 2.57 mmol, 0.1 eq), 4-Hydroxy TEMPO (0.44 g, 2.57 mmol, 0.1 eq) and solid NaCl (0.15 g, 2.57 mmol, 0.1 eq) was added to 25.0 ml of dichloromethane at 20° C. To this mixture, the 6,10-dimethylundeca-1,5,9-trien-4-ol obtained in example 1 (5.0 g, 25.7 mmol, 1 eq) was added and stirred for 3 hours at 20° C. under oxygen atmosphere (O$_2$ gas was continuously passed through the reaction mixture). The reaction was monitored by TLC and HPLC, which showed 50% conversion. After 3 hours of stirring an additional amount if nitric acid (70%) (0.22 g, 2.57 mmol, 0.1 eq), 4-Hydroxy TEMPO (0.44 g, 2.57 mmol, 0.1 eq) and NaCl (0.15 g, 2.57 mmol, 0.1 eq) was added again to reaction mixture at 20° C. and the reaction mixture was then stirred for additional 2 hours. After consumption of almost 95% starting material (based on TLC and HPLC), the reaction mixture was diluted by adding toluene (20.0 ml). Reaction mixture was filtered to remove inorganic materials and the filtrate was washed by saturated sodium thiosulfate solution (100.0 ml), 1N HCl (100.0 ml), saturated sodium bicarbonate solution (150.0 ml), brine (100.0 ml). The combined organic layer was dried over sodium sulfate and concentrated to afford 5.0 g of crude compound which was purified by vacuum distillation at 80° C./1.8 mbar to get 3.0 g (Yield: 60%) product.

$^1$HNMR (300 MHz, CDCl$_3$) (Mixture of E and Z isomers) δ 1.63 (s, 3H), 1.68 (s, 3H), 1.9 (s, 1H), 2.07-2.09 (m,4H), 2.50-2.55 (m, 0.5H), 3.09-3.14 (m,1.5H), 5.0-5.23 (m, 3H), 5.84-5.93 (m, 1H), 6.01 (bs, 1H).

Example 7

Synthesis of 1-(2,6,6-trimethylcyclohex-2-en-1-yl) but-2-en-1-one (α-damascone) (step c)

To a solution of 1-(2,6,6-trimethylcyclohex-2-en-1-yl) but-2-en-1-one (2 g, 10.4 mmol) in toluene (20 ml) was added phosphoric acid (1.52, 15 mmol) at room temperature and the mixture was then heated to 80° C. for 3 hours. Then reaction mixture was cooled to room temperature and then was quenched by adding water (20 ml). The aqueous layer was extracted by ethyl acetate (2×20 ml) and the combined organic layer was collected and dried over sodium sulfate and concentrated. The crude compound was purified by column chromatography to give 0.9 g of desired α-damascone in 45% yield.

$^1$HNMR (300 MHz, CDCl$_3$) δ 0.83 (s, 3H), 0.88 (s, 3H), 1.15-1.36 (m, 1H), 1.60 (brs, 3H), 1.64-1.78 (m, 1H), 1.92 (brd, 3H), 2.0-2.25 (m, 2H), 2.90 (s, 1H), 5.55-5.56 (bs, 1H), 6.25 (br d, 1H), 6.80-6.86 (m, 1H).

We claim:

1. A process for preparing 1-(2,6,6-trimethylcyclohex-2-en-1-yl)but-2-en-1-one, comprising:
   a) providing 6,10-dimethylundeca-1,5,9-trien-4-ol,
   b) oxidizing the 6,10-dimethylundeca-1,5,9-trien-4-ol provided in step a) with an oxidizing agent, which is selected from the group consisting of hypochlorites, hydrogen peroxide and molecular oxygen, in the presence of at least one organic nitroxyl radical, at least one nitrate compound and an inorganic solid, which is selected from the group consisting of alkali metal halides and alkali earth metal halides, to yield 6,10-dimethylundeca-1,5,9-trien-4-one,
   c) reacting the 6,10-dimethylundeca-1,5,9-trien-4-one obtained in step b) with an acid selected from mineral acids to yield 1-(2,6,6-trimethylcyclohex-2-en-1-yl) but-2-en-1-one.

2. The process of claim 1, where the total amount of the at least one nitroxyl radical used in step b) is in the range of 1 to 50 mol-%, based on the amount of 6,10-dimethylundeca-1,5,9-trien-4-ol in the reaction mixture.

3. The process according to claim 1, where the nitroxyl radical used in step b) is selected from the group consisting of (2,2,6,6-tetramethylpiperidin-1-yl)oxyl compounds, 2-azaadamantane-N-oxyl compounds, (1,1,3,3-tetramethyl-isoindolin-2-yl)oxyl compounds, 9-azanoradamantane N-oxyl, 9-azabicyclo[3.3.1]nonane N-oxyl, 2,2,5-trimethyl-4-phenyl-3-azahexane-3-nitroxide, diphenylnitroxyl, di-tert-butylnitroxyl and mixtures thereof.

4. The process of claim 1, where the nitrate compound used in step b) is selected from the group consisting of transition metal nitrates, nitric acid (HNO$_3$) and mixtures thereof.

5. The process of claim 1, where the nitrate compound used in step b) is selected from the group consisting of Fe(NO$_3$)$_3$ and nitric acid (HNO$_3$).

6. The process of claim 1, where the total amount of the at least one nitrate compound used in step b) is in the range of 1 to 50 mol-%, based on the amount of 6,10-dimethylundeca-1,5,9-trien-4-ol in the reaction mixture.

7. The process of claim 1, where the molar ratio of the at least one nitroxyl radical to the at least one nitrate compound used in step b) is in the range of 1:10 to 10:1.

8. The process of claim 1, where the inorganic solid used in step b) is selected from the group consisting of LiF, LiCl, KF, KCl, NaF, NaCl and mixtures thereof.

9. The process of claim 1, where the total amount of the inorganic solid used in step b) is in the range of 0.5 to 20% by weight, based on the amount of 6,10-dimethylundeca-1,5,9-trien-4-ol in the reaction mixture.

10. The process of claim 1, where the oxidizing agent used in step b) is molecular oxygen.

11. The process of claim 1, where the oxidizing agent used in step b) is present in excess, based on the amount of 6,10-dimethylundeca-1,5,9-trien-4-ol in the reaction mixture.

12. The process of claim 1, where the acid used in step c) is selected from sulfuric acid and phosphoric acid.

13. The process of claim 1, where the total amount of the acid used in step c) is in the range of 0.9 to 5 mol per 1 mol of 6,10-dimethylundeca-1,5,9-trien-4-one.

14. The process of claim 1, where the at least one nitroxyl radical, the at least one nitrate compound and the inorganic solid are added to 6,10-dimethylundeca-1,5,9-trien-4-ol provided in step a).

15. The process of claim 1, where the 6,10-dimethylundeca-1,5,9-trien-4-ol is provided by reacting 3,7-dimethylocta-2,6-dienal with an allylmagnesium compound.

\* \* \* \* \*